US009623377B2

(12) United States Patent
Yezerets et al.

(10) Patent No.: US 9,623,377 B2
(45) Date of Patent: Apr. 18, 2017

(54) SYSTEMS AND METHODS FOR REDUCING SECONDARY EMISSIONS FROM CATALYST COMPONENTS

(75) Inventors: Aleksey Yezerets, Columbus, IN (US); Z. Gerald Liu, Madison, WI (US); Krishna Kamasamudram, Columbus, IN (US); Neal W. Currier, Columbus, IN (US)

(73) Assignee: Cummins Inc., Columbus, IN (US)

(*) Notice: Subject to any disclaimer, the term of this patent is extended or adjusted under 35 U.S.C. 154(b) by 584 days.

(21) Appl. No.: 13/551,723

(22) Filed: Jul. 18, 2012

(65) Prior Publication Data
US 2014/0023576 A1 Jan. 23, 2014

(51) Int. Cl.
*B01D 53/56* (2006.01)
*B01D 53/94* (2006.01)
*F01N 3/10* (2006.01)
*F01N 11/00* (2006.01)
*F01N 3/021* (2006.01)
*F01N 3/035* (2006.01)
*F01N 13/00* (2010.01)
*F01N 3/20* (2006.01)
*F01N 3/36* (2006.01)

(52) U.S. Cl.
CPC ..... *B01D 53/9495* (2013.01); *B01D 53/9436* (2013.01); *F01N 3/021* (2013.01); *F01N 3/035* (2013.01); *F01N 3/106* (2013.01); *F01N 11/002* (2013.01); *F01N 13/009* (2014.06); *B01D 53/944* (2013.01); *B01D 53/9418* (2013.01); *B01D 2255/2022* (2013.01); *B01D 2255/2027* (2013.01); *B01D 2255/2092* (2013.01); *B01D 2255/20723* (2013.01); *B01D 2255/904* (2013.01); *B01D 2258/012* (2013.01); *F01N 3/208* (2013.01); *F01N 3/36* (2013.01); *F01N 2560/08* (2013.01); *F01N 2900/1616* (2013.01); *Y02T 10/24* (2013.01); *Y02T 10/47* (2013.01)

(58) Field of Classification Search
None
See application file for complete search history.

(56) References Cited

U.S. PATENT DOCUMENTS

| | | |
|---|---|---|
| 5,057,205 A | 10/1991 | Chin et al. |
| 7,062,904 B1 | 6/2006 | Hu et al. |
| 7,264,785 B2 | 9/2007 | Blakeman et al. |
| 7,611,680 B2 | 11/2009 | Jia et al. |

(Continued)

FOREIGN PATENT DOCUMENTS

| | | |
|---|---|---|
| EP | 2 103 670 A2 | 9/2009 |
| WO | 2012051273 A1 | 4/2012 |

OTHER PUBLICATIONS

International Search Report and Written Opinion, PCT/US2013/050233, ISA/US, Cummins Inc. Dec. 23, 2013.

*Primary Examiner* — Jennifer A Smith
*Assistant Examiner* — Anita Nassiri Motlagh
(74) *Attorney, Agent, or Firm* — Taft Stettinius & Hollister LLP

(57) ABSTRACT

System and methods for reducing secondary emissions in an exhaust stream from an internal combustion engine are disclosed. The systems and methods include a filtration device positioned downstream from an SCR catalyst of an aftertreatment system disposed in the exhaust system. The filtration device can also be used for particulate filter diagnostics and for treatment of ammonia slip.

12 Claims, 3 Drawing Sheets

(56) References Cited

U.S. PATENT DOCUMENTS

| | | |
|---|---|---|
| 2010/0175372 A1 | 7/2010 | Lambert et al. |
| 2010/0192546 A1* | 8/2010 | Nohl .............................. 60/286 |
| 2010/0236224 A1* | 9/2010 | Kumar et al. ................. 60/297 |
| 2011/0047973 A1 | 3/2011 | Wilhelm et al. |
| 2011/0061367 A1* | 3/2011 | Laermann et al. ............ 60/277 |
| 2011/0138789 A1* | 6/2011 | Chapman ....................... 60/302 |
| 2011/0277454 A1 | 11/2011 | Christianson et al. |
| 2012/0023911 A1 | 2/2012 | Liu |

* cited by examiner

SYSTEMS AND METHODS FOR REDUCING SECONDARY EMISSIONS FROM CATALYST COMPONENTS

BACKGROUND

The present application generally relates to exhaust aftertreatment systems, and more particularly, but not exclusively, to selective catalytic reduction ("SCR") systems.

Presently available SCR systems adsorb ammonia ($NH_3$) on a catalyst and then react the $NH_3$ with $NO_x$ to reduce the $NO_x$ emissions. The $NH_3$ is typically stored as a less reactive composition, e.g. urea, and hydrolyzed into $NH_3$ in the exhaust system as required to reduce the $NO_x$ emitted by the engine. At certain system operating conditions, the catalyst may produce secondary emissions of catalytic material. The possibility of emission of catalytic material has led to resistance of adoption of certain types of SCR catalysts, such as vanadium based SCR catalysts. In addition, SCR systems are known to create "ammonia slip" in which ammonia that does not adsorb slips through the SCR catalyst.

SCR systems also typically employ a diesel particulate filter upstream of the SCR catalyst. Available techniques for diesel particulate filter ("DPF") diagnostics suffer from a number of disadvantages, drawbacks and inadequacies including an inability to adequately diagnose DPF loading and loss of filtration efficiency among others.

Therefore, a need remains for systems and methods for treating secondary emissions, including those comprising catalytic material and ammonia slip. A need also remains for improving diagnostic capabilities of diesel particulate filter conditions.

SUMMARY

One embodiment is a unique system, method and device to reduce secondary emissions from an exhaust of an internal combustion engine. Another embodiment is a unique system, method and device to provide an onboard diagnostic capability for a diesel particulate filter. Further embodiments, forms, objects, features, advantages, aspects, and benefits shall become apparent from the following description and drawings.

DESCRIPTION OF THE ILLUSTRATIVE EMBODIMENTS

Figure 1:
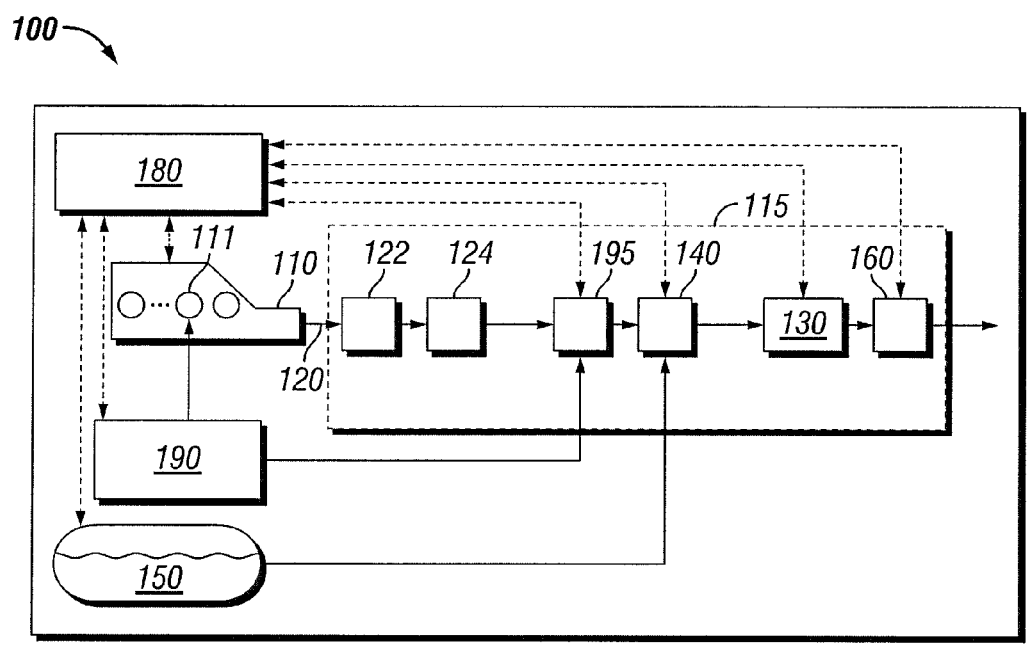
FIG. 1 is a schematic illustration of a system including an exemplary aftertreatment system.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated embodiments, and any further applications of the principles of the invention as illustrated therein as would normally occur to one skilled in the art to which the invention relates are contemplated herein.

With reference to FIG. 1, there is illustrated a system 100 including an engine 110 which is configured to provide rotating mechanical power to system 100 and to output exhaust to an exhaust flow path 120. System 100 is illustrated schematically and may be included with a car, truck, bus, boat, recreational vehicle, construction equipment or another type of vehicle. Other embodiments include an engine provided in non-vehicular applications such as a generator set. The exhaust output by engine 110 includes $NO_x$ and other components which are to be reduced using an exhaust aftertreatment system 115. In certain implementations, the system 100 includes an exhaust gas recirculation (EGR) line (not shown) configured to allow a portion of the exhaust gas generated by the engine to recirculate back into the engine for altering the combustion properties of the engine 110.

In one embodiment, exhaust aftertreatment system 115 may include an oxidation catalyst 122 which is in fluid communication with exhaust flow path 120 and is operable to catalyze oxidation of one or more compounds in exhaust flowing through exhaust flow path 120, for example, oxidation of unburned hydrocarbons or oxidation of NO to $NO_2$. Oxidation catalyst 122 can be any of various flow-through oxidation catalysts. Generally, oxidation catalyst 122 includes a substrate with an active catalyst layer configured to oxidize at least some particulate matter (e.g., the soluble organic fraction of soot) in the exhaust and reduce unburned hydrocarbons and CO in the exhaust to less environmentally harmful compounds. For example, in some implementations, the oxidation catalyst 122 may sufficiently reduce the hydrocarbon and CO concentrations in the exhaust to meet the requisite emissions standards.

Exhaust aftertreatment system 115 also includes a diesel particulate filter 124 in fluid communication with exhaust flow path 120 and operable to reduce the level of particulates in exhaust flowing through exhaust flow path 120. In an exemplary embodiment diesel particulate filter 124 is a catalyzed soot filter. The diesel particulate filter 124 can be any of various particulate filters known in the art configured to reduce particulate matter concentrations, e.g., soot and ash, in the exhaust gas to meet requisite emission standards. The diesel particulate filter 124 includes a filter substrate that captures soot and other particulate matter generated by the engine 110. The system 100 periodically regenerates diesel particulate filter 124 to remove particulate matter that has accumulated on the diesel particulate filter over time. For example, diesel particulate filter 124 can be regenerated by increasing the temperature of the exhaust gas above a threshold temperature corresponding with combustion of the particulate matter.

Exhaust aftertreatment system 115 may include a reductant injector 140 and an SCR catalyst 130 downstream from particulate filter 124. Reductant injector 140 is supplied with reductant from a reductant reservoir 150 and is operable to inject reductant into exhaust flow path 120. In an exemplary embodiment the reductant is an aqueous solution of urea which decomposes to provide ammonia. Other embodiments utilize different reductants, for example, aqueous solutions of ammonia, anhydrous ammonia, or other reductants suitable for SCR. Reductant injected into exhaust flow path 120 is provided to SCR catalyst 130 which is in flow communication with exhaust flow path 120 and is operable to catalyze the reduction of $NO_x$. Like the filter substrate of the diesel particulate filter 124, the SCR catalyst 130 can be subject to high temperatures, such as during a regeneration event on the diesel particulate filter 124.

In certain embodiments, the SCR catalyst 130 includes a vanadium based catalyst. Vanadium based SCR systems can be attractive commercially since less expensive oxidation catalysts may be employed in aftertreatment system when compared to, for example, zeolite based SCR systems. However, at high temperatures, such as occur during regeneration of diesel particulate filter 124, the vanadium based SCR catalyst may produce secondary emissions of catalytic material. Thus, adoption of vanadium based SCR systems in the United States has been hampered over environmental concerns associated with secondary emissions of catalytic material under such high-temperature conditions. For other embodiments, the SCR catalyst 130 can be any of various catalysts known in the art. For example, in some implementations, the SCR catalyst is a zeolite based catalyst, such as a Cu-Zeolite or a Fe-Zeolite catalyst.

Exhaust aftertreatment system 115 may further include a hydrocarbon (HC) injector 195 which is supplied with HC from an HC reservoir 190 and is operationally coupled to the exhaust stream at a position upstream of SCR catalyst 130. HC reservoir may also be coupled to a cylinder 111 of engine 110. Other embodiments of system 100 may include an engine 110 having a common rail fuel system capable of injecting a post injection fuel where at least a portion of the post injection fuel does not combust to provide HC in the exhaust stream. Embodiments are also contemplated without a HC injector.

Downstream from SCR catalyst 130 there is provided a secondary emission reduction device 160. In one embodiment, reduction device 160 is a filter or filter substrate arranged to capture secondary emissions from, for example, SCR catalyst 130. Reduction device 160 is positioned at a location sufficiently spaced from SCR catalyst 130 so that exhaust stream temperatures at reduction device 160 are less than at SCR catalyst 130. Positioning reduction device 160 in a lower temperature region of aftertreatment system 115 permits condensation of volatized catalyst particles on the filter of reduction device 160. In still other embodiments, reduction device 160 includes a mesh screen structure or filter coated with a material that physically and/or chemically enhances capture and retention of volatized catalyst particles on reduction device 160. Examples of suitable coating materials include high surface area $\gamma$-$Al_2O_3$ and salts of potassium or sodium.

Each of the catalyst or filter substrates of the oxidation catalyst 122, diesel particulate filter 124, and SCR catalyst 130 are subject to at least partially fail or deteriorate due to any of various conditions. For example, high exhaust temperature events such as during diesel particulate filter regeneration, vibratory stresses, and aging of components can lead to a substrate failure or deterioration where pieces or particles associated with the component are emitted through the exhaust flow. Reduction device 160 captures such pieces and particles prior to emission into the environment to reduce or eliminate secondary emissions from one or more of these components.

Exhaust flow path 120, as illustrated schematically in FIG. 1, may be provided in a variety of physical configurations. In an exemplary embodiment an exhaust flow path proceeds from the output of a turbocharger (not shown) of engine 110 through a conduit to a structure containing oxidation catalyst 122 and diesel particulate filter 124, through a second conduit to a structure containing SCR catalyst 130 and through another conduit to reduction device 160, which outlets to the ambient environment. Reduction device 160 is a filter in one embodiment that carries an ammonia oxidation catalyst. Since reduction device 160 is located at a position downstream of the SCR catalyst 130, the reduction device 160 can also provide a filtered ammonia oxidation catalyst which is operable to catalyze the reaction of $NH_3$ which slips from the SCR catalyst 130.

Figure 2A:
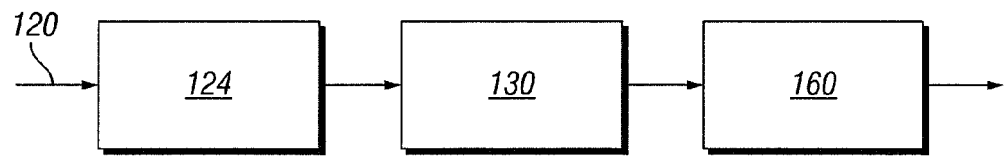
FIGS. 2A and 2B are schematic illustrations of subsystems included in an exemplary aftertreatment system.

In other embodiments, the components of the exhaust gas after-treatment system 115 can be positioned in any of various arrangements, and the system can include other components or fewer components. For example, FIG. 2A illustrates an embodiment of exhaust gas aftertreatment system 115 with diesel particulate filter 124, SCR catalyst 130 downstream from diesel particulate filter 124, and secondary emission reduction device 160 downstream from SCR catalyst 130. Generally, exhaust gas treated in the exhaust gas after-treatment system 115 and released into the atmosphere consequently contains significantly fewer pollutants, such as diesel particulate matter, $NO_x$, and hydrocarbons, such as carbon monoxide and carbon dioxide, than untreated exhaust gas.

Referring back to system 100 in FIG. 1, in certain embodiments, system 100 includes a controller 180 which functionally executes certain operations for engaging aftertreatment system 115 and/or system 100. Controller 180 forms a portion of a processing subsystem including one or more computing devices having memory as well as a number of inputs and outputs for interfacing with various sensors and systems of system 100. Controller 180 can be an electronic circuit comprised of one or more components, including digital circuitry, analog circuitry, or both. Controller 180 may be a single device or a distributed device. Controller 180 may include one or more control algorithms defined by operating logic in the form of software instructions, hardware instructions, firmware instructions, dedicated hardware, or the like.

In one form, controller 180 is of a programmable microcontroller solid-state integrated circuit type that includes memory and one or more central processing units. The memory of controller 180 includes of one or more components and can be of any of volatile or nonvolatile, solid-state, optical media, magnetic media, combinations of these, or other types of memory. Controller 180 can include signal conditioners, signal format converters (such as analog-to-digital and digital-to-analog converters), limiters, clamps, filters, and the like as needed to perform various control and regulation operations described herein. Controller 180, in an exemplary embodiment, may be a type of controller sometimes referred to as an electronic or engine control module (ECM), electronic or engine control unit (ECU) or the like, that is directed to the regulation and control of engine operation. Alternatively, controller 180 may be dedicated to the control of just the operations described herein or to a subset of controlled aspects of system 100.

Figure 2B:
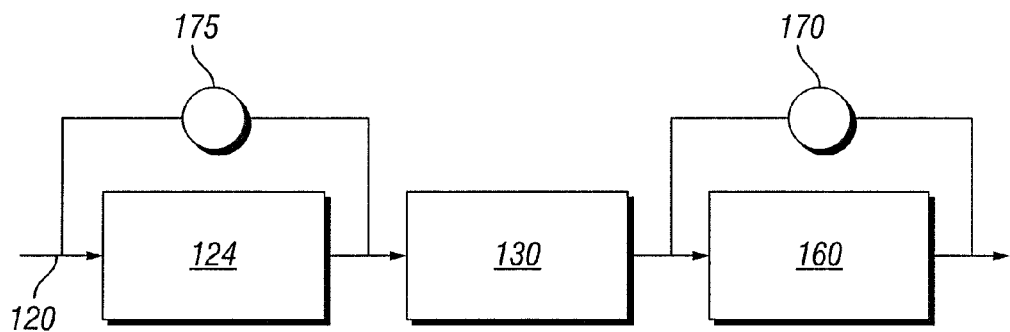

Controller 180 is in operative communication with a differential pressure sensor 170 (FIG. 2B) which provides controller 180 with information indicative of the pressure drop across reduction device 160. In a further embodiment, controller 180 is in operative communication with a differential pressure sensor 175 (FIG. 2B) which provides controller 180 with information indicative of the pressure drop across diesel particulate filter 124. Controller 180 may also be in operative communication with one or more temperature sensors that indicate temperature of the exhaust system. In other embodiments, information from temperature sensors, flow sensors, pressure sensors, and $NO_x$ sensors in various locations is utilized to determine information indicative of the conditions of SCR catalyst 130 and/or the exhaust system. Controller 180 may also be in operative communication with HC injector 195 and HC reservoir 190, and/or reductant injector 140 and reservoir 150 for treatment of exhaust gases as known in the art.

Differential pressure sensor 170 is fluidly coupled to the exhaust flowpath 120 at a first position upstream of the reduction device 160 and at a second position downstream of reduction device 160. A second differential pressure sensor 175 can be fluidly coupled to the exhaust flowpath 120 at a first position upstream of diesel particulate filter 124 and at a second position downstream of the diesel particulate filter 124. The differential pressure sensors 170, 175 may be a single pressure transducer, multiple pressure transducers, a single electromechanical pressure sensor, two inductive pressure sensors or any other combination of pressure sensor(s) that can be configured to determine a pressure drop across the reduction device 160 and/or diesel particulate filter 124. This pressure drop may be conveyed from the differential pressure sensor 170, 175 as a pressure value, multiple pressure values where a difference can be taken, a voltage which may be converted to a pressure value, and/or a digital signal which can be read by a processor or processor subsystem and is correlated to a pressure value.

Controller 180 is operable to determine if a pressure drop of the exhaust gas stream across reduction device 160 is indicative of a failure of diesel particulate filter 124. For example, during normal operation with an operations particulate filter 124, the pressure drop across reduction device 160 is relatively small since diesel particulate filter 124 filters the particulate matter from the exhaust stream. A failure of particulate filter 124 causes reduction device 160 to receive the particulates from the exhaust stream, thus causing a substantial increase in the pressure drop across reduction device 160. When pressure sensor 170 provides an indication of that the pressure drop across reduction device 160 has increased by more than a predetermined threshold, then controller 180 is operable to determine if the pressure change is indicative of a failure of diesel particulate filter 124 and provide a communication to an onboard diagnostic system regarding the same.

Controller 180 may also be operable to determine if a pressure drop of the exhaust gas stream across diesel particulate filter 124 indicated by differential pressure sensor 175 is indicative of a failure of diesel particulate filter 124. Controller 180 can be operatively linked to an onboard diagnostics system to provide an indication of diesel particulate filter failure based on one or both of the pressure drop signals provided by sensor 170 and/or sensor 175.

In certain embodiments, the controller 180 includes one or more modules structured to functionally execute the operations of the controller 180. The description herein including modules emphasizes the structural independence of the aspects of the controller, and illustrates one grouping of operations and responsibilities of the controller 180. Other groupings that execute similar overall operations are understood within the scope of the present application. Modules may be implemented in hardware and/or software on computer readable medium, and modules may be distributed across various hardware or software components.

Controller 180 is in operative interconnection with various elements of system 100 as illustrated in FIG. 1 with dashed lines extending between controller 180 and various elements of system 100. These operative interconnections may be implemented in a variety of forms, for example, through input/output interfaces coupled via wiring harnesses, a datalink, a hardwire or wireless network and/or a lookup from a memory location. In other instances all or a portion of the operative interconnection between controller 180 and an element of system 100 may be virtual. For example, a virtual input indicative of an operating parameter may be provided by a model implemented by controller 180 or by another controller which models an operating parameter based upon other information.

Figure 3:
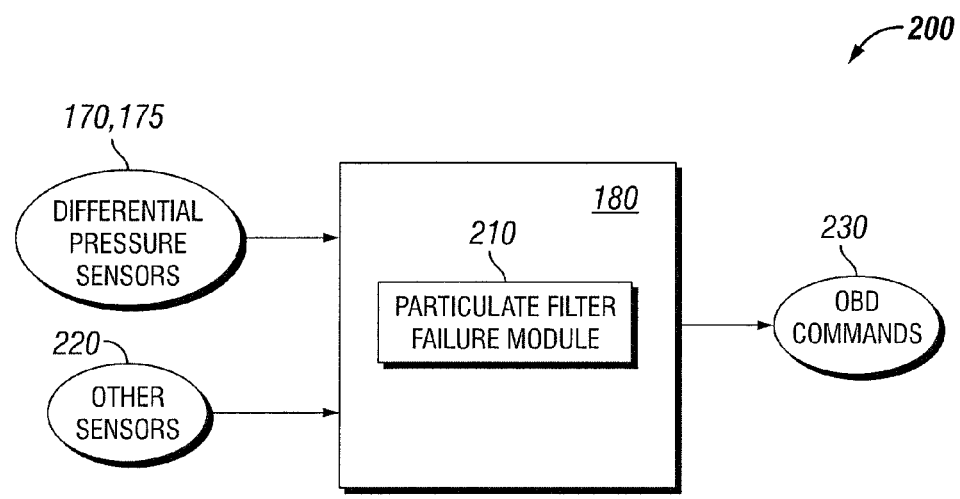
FIG. 3 is a diagram illustrating an exemplary control operation for an aftertreatment procedure.

FIG. 3 represents an apparatus 200 that includes controller 180 with various components illustrated as representative modules, inputs, outputs, and intermediate data parameters. According to one embodiment, the controller 180 includes a particulate filter failure detection module 210 configured to determine a failure condition of diesel particulate filter 124. For example, the particulate filter failure condition module 210 may be configured to determine a failure condition for the diesel particulate filter 124.

The particulate filter failure detection module 210 can use any of various methods and techniques for determining the particulate matter loads associated with diesel particulate filter 124. For example, in certain implementations, the controller 180 receives input from the differential pressure sensor 170 indicating a pressure difference across reduction device 160. In further implementations, controller 180 also receives input from the differential pressure sensor 175 across diesel particulate filter 124. Additionally, the controller 180 may receive other input regarding any of various conditions of the system 100, such as exhaust flow rates, exhaust temperatures, exhaust component mass concentrations, from other sensors 220. In one specific implementation, based on the input from the differential pressure sensor 170, the respective exhaust gas flow rates through the diesel particulate filter 124, and/or the other sensed operating conditions, the particulate filter failure detection module 210 can determine a failure condition for diesel particulate filter 124. In another specific implementation, based on the input from the differential pressure sensor 170 and differential pressure sensor 175, the respective exhaust gas flow rates through the diesel particulate filter 124, and/or the other sensed operating conditions, the particulate filter failure detection module 210 can determine a failure condition for diesel particulate filter 124.

A failure condition for diesel particulate filter 124 can be triggered in any of various ways. For example, a determination by the particulate filter failure module 210 of a substantial increase in the pressure drop across reduction device 160 indicates that reduction device 160 is accumulating particles from the exhaust gas normally captured by diesel particulate filter 124. Therefore, a pressure drop increase across reduction device 160 can be measured by sensor 170 and provide an indication that diesel particulate filter 124 is not properly functioning to filter particulates from the exhaust gas when the pressure drop increase exceeds a predetermined threshold.

In another example, a failure event can be registered based on a particulate matter load estimate determined by the particulate filter failure module 210 after a regeneration event. More specifically, a particulate matter load estimate determines that a pressure drop across diesel particulate filter 124 exceeds a predetermined threshold after a regeneration event such that regeneration is not sufficient to provide an operational diesel particulate filter 124.

Alternatively, or additionally, in certain embodiments, the failure event can be determined by a differential pressure across diesel particulate filter 124 falling below a predetermined threshold, indicating the lack of an operational filtering element in exhaust flow path 120. This determination can be coupled with a determination of an increased pressure differential across secondary device 160 indicating that secondary device 160 is being loaded with particles from the exhaust stream normally captured by diesel particulate filter 124. In one particular embodiment, a first absolute pressure sensor upstream of diesel particulate filter 124 and a second absolute pressure sensor between diesel particulate filter 124 and reduction device 160 provide a diesel filter diagnostic capability. For example, a determination that a pressure difference between the two absolute pressure sensors is less than a predetermined threshold can provide an indication that diesel particulate filter 124 is non-operational due the lack of back pressure being created by diesel particulate filter 124.

The failure of diesel particulate filter 124 can be communicated by controller 180 to an onboard diagnostics system (not shown) via OBD commands 230. The OBD commands 230 provide a signal to the operator, service personnel, or others that a service condition for diesel particulate filter 124 exists.

The schematic flow diagram and related description which follows provides an illustrative embodiment of performing procedures for engaging a diesel particulate filter diagnostic system. Operations illustrated are understood to be exemplary only, and operations may be combined or divided, and added or removed, as well as re-ordered in whole or part. Certain operations illustrated may be implemented by a computer executing a computer program product on a computer readable medium, where the computer program product comprises instructions causing the computer to execute one or more of the operations, or to issue commands to other devices to execute one or more of the operations.

Figure 4:
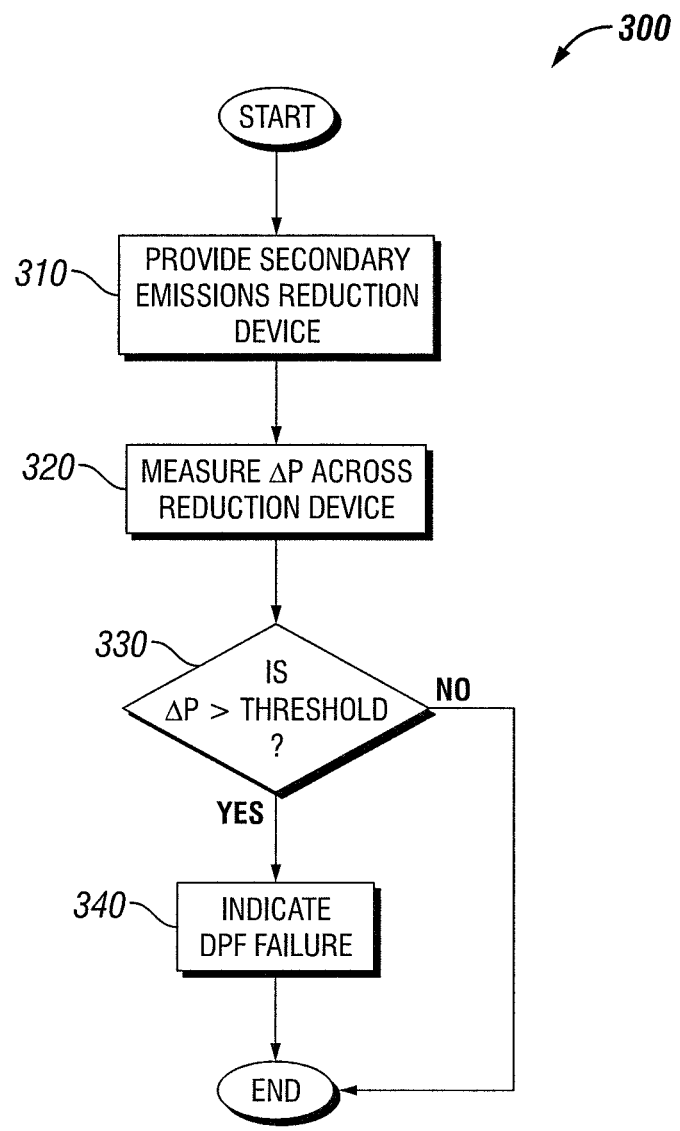
FIG. 4 is a flow diagram of a procedure that can be performed with an aftertreatment system.

Referencing FIG. 4, a process 300 includes an operation 310 to provide a secondary emission reduction device downstream of a selective catalytic reduction (SCR) catalyst as part of an exhaust stream of an engine. The secondary emission reduction device can be, as discussed above, a filter that also includes a coating of any known material suitable as an ammonia oxidation catalyst. The process 300 further includes an operation 320 in which the pressure drop across the secondary emission reduction device is measured at periodic intervals.

Conditional 330 determines if a pressure drop across reduction device 160 is more than a pressure drop threshold indicative of failure of particulate filter 124. During normal operation of aftertreatment system 115, the pressure drop across reduction device 160 is relatively small since particulate filter 124 has removed particulates from the exhaust stream. A failure of particulate filter 124 permitting particulates to pass therethrough results in particulates being accumulated on reduction device 160, thereby causing a pressure drop increase across reduction device 160. Conditional 330 determines if the pressure drop increase is greater than a predetermined threshold, where the predetermined threshold is greater than a range of pressure drops across reduction device 160 expected during normal operation. These values may be set values in a look up table and/or may be determined by a calculation with retrieved variables.

If the response to conditional 330 is a YES, then procedure 300 continues at operation 340. At operation 340 a signal indicating a failure or service condition for particulate filter 124 is provided to an onboard diagnostics system of the vehicle. If the response to conditional 330 is a NO, then procedure 300 ends until started again after lapse of a predetermined amount of time and/or occurrence of one or more operating conditions.

As is evident from the figures and text presented above, a variety of embodiments according to the present invention are contemplated.

One embodiment is a method, including: (1) providing a selective catalytic reduction (SCR) catalyst disposed in an exhaust stream of an internal combustion engine; (2) providing a diesel particulate filter upstream of the SCR catalyst; (3) providing a secondary emission reduction device downstream of the SCR catalyst; (4) determining that a pressure drop across the secondary emission reduction device exceeds a predetermined threshold; and (5) providing a signal indicating failure of the diesel particulate filter when the pressure drop exceeds the threshold.

As a further feature, determining that the pressure drop of the exhaust stream across the secondary emission device exceeds the threshold may include: measuring the differential pressure across the secondary emission reduction device; measuring the absolute pressure of the exhaust steam upstream of the diesel particulate filter and between the diesel particulate filter and the secondary emission reduction device; and measuring the pressure drop across the diesel particulate filter.

Another embodiment includes a system with a selective catalytic reduction (SCR) catalyst disposed in an exhaust stream of an internal combustion engine; a diesel particulate filter in the exhaust stream upstream from the SCR catalyst; and a secondary emission reduction device in the exhaust stream downstream from the SCR catalyst. In one form, the secondary emission reduction device includes a filter to capture secondary emissions from a vanadium based SCR catalyst. The filter may include one or more coatings or surface area treatments to physically or chemically enhance capture and retention of volatized catalyst components. In another form, the secondary emission reduction device includes a filter that is a carrier for an ammonia slip catalyst.

Another embodiment of the system includes a controller structured to determine that a failure condition for the diesel particulate filter has occurred. This embodiment may further include the controller providing an onboard diagnostic signal indicative of the failure.

The controller of this embodiment may be further structured to determine that a pressure drop of the exhaust stream across a secondary emission reduction device is more than a threshold indicative of a diesel particulate filter failure upstream of the secondary device.

Further features of this embodiment may include the afterteatment system having a differential pressure sensor at the secondary emission reduction device. In a further refinement, a differential pressure sensor is provided at the diesel particulate filter.

While the invention has been illustrated and described in detail in the drawings and foregoing description, the same is to be considered as illustrative and not restrictive in character, it being understood that only certain exemplary embodiments have been shown and described and that all changes and modifications that come within the spirit of the inventions are desired to be protected. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. A system for reducing secondary emissions from an internal combustion engine, comprising:
    a diesel particulate filter in fluid communication with an exhaust flowpath from the internal combustion engine;
    an SCR catalyst in fluid communication with the exhaust flowpath downstream from the diesel particulate filter;
    a secondary emission reduction device including a filter in fluid communication with the exhaust flowpath downstream from the SCR catalyst, wherein the filter is in a temperature region of the exhaust flowpath that is lower than that of the SCR catalyst to permit condensation of volatized of catalytic material from the SCR catalyst on the filter, wherein the secondary emission reduction device includes an ammonia oxidation catalyst to catalyze ammonia slip from the SCR catalyst;
    a first differential pressure sensor operable to determine a pressure drop of exhaust gas in the exhaust flowpath across the secondary emission reduction device;
    a second differential pressure sensor operable to determine a pressure drop of exhaust gas in the exhaust flowpath across the diesel particulate filter; and
    a controller operatively connected to the first differential pressure sensor and to the second differential pressure sensor, wherein the controller is configured to determine a failure condition of the diesel particulate filter from the pressure drop across the diesel particulate filter falling below a first predetermined threshold in conjunction with the pressure drop across the secondary emission reduction device exceeding a second predetermined threshold and provide an onboard diagnostic command corresponding to the failure of the diesel particulate filter.

2. The system of claim 1, wherein the filter is coated with the ammonia oxidation catalyst to catalyze oxidation or removal of ammonia slip from the SCR catalyst.

3. The system of claim 1, wherein the SCR catalyst is a vanadium based catalyst.

4. The system of claim 1, wherein the filter of the secondary emission reduction device includes a material coating to enhance filtering of volatized SCR catalyst components.

5. The system of claim 4, wherein the material coating includes at least one of sodium, potassium or γ-Al$_2$O$_3$.

6. A system, comprising:
    a diesel particulate filter in fluid communication with an exhaust flowpath from the internal combustion engine;
    an SCR catalyst in fluid communication with the exhaust flowpath downstream from the diesel particulate filter;
    a secondary emission reduction device including a filter in fluid communication with the exhaust flow downstream from the SCR catalyst, wherein the filter is in a temperature region of the exhaust flowpath that is lower than that of the SCR catalyst to permit condensation of volatized catalytic material from the SCR catalyst on the filter;
    a controller structured to:
        to determine a pressure drop across the diesel particulate filter and compare the pressure drop to a first predetermined threshold;
        to determine a pressure drop across the secondary emission reduction device and compare the pressure drop to a second predetermined threshold; and
        provide an onboard diagnostic command indicating diesel particulate filter failure in response to the pressure drop across the diesel particulate filter being less than the first predetermined threshold in conjunction with the pressure drop across the secondary emission reduction device being more than the second predetermined threshold.

7. The system of claim 6, wherein the secondary emission reduction device includes an ammonia oxidation catalyst to catalyze ammonia slip from the SCR catalyst.

8. The system of claim 6, wherein the SCR catalyst is a vanadium based catalyst.

9. The system of claim 8, wherein the filter of the secondary emission reduction device includes a material coating to enhance filtering of volatized SCR catalyst components.

10. The system of claim 9, wherein the material coating includes at least one of sodium, potassium or γ-Al$_2$O$_3$.

11. The system of claim 6, wherein the diesel particulate filter failure corresponds to an inability of the diesel particulate filter to remove particulates from the exhaust stream.

12. The system of claim 1, wherein the failure of the diesel particulate filter corresponds to an inability of the diesel particulate filter to remove particulates from the exhaust stream.

* * * * *